(12) United States Patent
Diehl

(10) Patent No.: US 7,744,740 B2
(45) Date of Patent: Jun. 29, 2010

(54) PROCEDURE TO RECOGNIZE THE DIFFUSION GAS COMPOSITION IN A WIDEBAND LAMBDA SENSOR

(75) Inventor: Lothar Diehl, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 850 days.

(21) Appl. No.: 11/605,988

(22) Filed: Nov. 28, 2006

(65) Prior Publication Data

US 2007/0119719 A1    May 31, 2007

(30) Foreign Application Priority Data

Nov. 28, 2005   (DE) ....................... 10 2005 056 515

(51) Int. Cl.
  *G01N 27/419* (2006.01)
  *G01N 27/417* (2006.01)
  *G01N 27/407* (2006.01)
  *G01N 27/409* (2006.01)
  *G01N 27/41* (2006.01)

(52) U.S. Cl. ................. 205/784.5; 205/785; 205/785.5; 205/782; 205/783; 205/784

(58) Field of Classification Search ............. 205/782, 205/783, 784, 784.5, 785, 785.5
See application file for complete search history.

(56) References Cited

U.S. PATENT DOCUMENTS

| 6,280,605 | B1 * | 8/2001 | Jach et al. ................. 205/784.5 |
| 2001/0050229 | A1 * | 12/2001 | Schnaibel et al. ........... 204/421 |
| 2005/0173265 | A1 * | 8/2005 | Stahl ....................... 205/783.5 |
| 2005/0252771 | A1 * | 11/2005 | Wiedenmann et al. ...... 204/426 |
| 2006/0207244 | A1 * | 9/2006 | Handler et al. .................. 60/295 |
| 2006/0289314 | A1 * | 12/2006 | Schnaibel et al. ........... 205/782 |

FOREIGN PATENT DOCUMENTS

DE    199 12 102 A1   10/2000

* cited by examiner

*Primary Examiner*—Bruce F Bell
(74) *Attorney, Agent, or Firm*—Merchant & Gould P.C.

(57) ABSTRACT

In a procedure to recognize the gas composition of a gas mixture, which consists of at least two gases of preferably different diffusion properties, delivered to a wideband lambda sensor, especially a gas mixture of an exhaust gas of an internal combustion engine of a motor vehicle, whereby the lambda sensor has a pumping cell with at least one gas measurement chamber, provision is made for the recognition of the gas composition of the gas mixture to result by means of modulation of the gas in the gas measurement chamber. Preferably the air number in the gas measurement chamber of the pumping cell is periodically altered, whereby the sensitivity of the lambda sensor to the gases, of which there are at least two, likewise periodically changes.

10 Claims, 4 Drawing Sheets

FIG.3A (STATE OF THE ART)

PROCEDURE TO RECOGNIZE THE DIFFUSION GAS COMPOSITION IN A WIDEBAND LAMBDA SENSOR

The invention concerns generally the area of exhaust gas aftertreatment especially in regard to motor vehicles driven by internal combustion and particularly a procedure to recognize the gas composition of a gas delivered to a wideband lambda sensor.

BACKGROUND OF THE INVENTION

A closed-loop lambda control is, in connection with a catalytic converter, today the most effective emission control procedure for the gasoline engine. Low exhaust gas values can be achieved only through interaction with ignition and injection systems available today. The deployment of a three way catalytic converter or a selective catalytic converter is especially effective. This type of catalytic converter has the quality to reduce hydrocarbons, carbon monoxide and nitrogen oxides up to more than 98% in the instance that the engine is driven in a range of approximately 1% around the stoichiometric air-fuel-ratio with LAMBDA=1. In so doing, the variable LAMBDA also denoted as "air number" indicates how far the actual air-fuel-mixture at hand deviates from the value LAMBDA=1, which corresponds to a theoretically necessary mass ratio for complete combustion of 14.7 kg air to 1 kg gasoline, i.e. LAMBDA is the quotient from the air mass delivered and the theoretical air supply, which is needed.

In the closed-loop lambda control the respective exhaust gas is measured and the amount of fuel delivered is corrected immediately corresponding to the measurement result by means of, for example, the fuel injection system. A lambda sensor is used as a probe, which has a voltage jump exactly at LAMBDA=1 and in this way delivers a signal, which indicates if the mixture is richer or leaner than LAMBDA=1. The mode of operation of the lambda sensor is based on the principle of a galvanic oxygen concentration cell with a solid electrolyte.

Lambda sensors designed as two-point sensors work in an inherently known manner according to the Nernst principle, and in fact based on a Nernst cell. The solid electrolyte consists of two border surfaces separated by a ceramic surface. The ceramic material used becomes conductive for oxygen ions at approximately 350° C., so that the so-called Nernst voltage is produced then on both sides of the ceramic surface when the oxygen proportion is different. This electrical voltage is a measurement for the difference of the oxygen proportions on both sides of the ceramic surface. Because the residual oxygen content in the exhaust gas of an internal combustion engine is dependent to a great degree on the air-fuel-ratio of the mixture delivered to the engine, it is possible to use the oxygen proportion in the exhaust gas as a measurement for the actual existing air-fuel-ratio.

In the so-called wideband sensors, the probe is designed as the wideband sensor. This is formed from solid electrolyte layers as well as from a number of electrodes. Such a construction proceeds from the German patent DE 19 912 102 A1, especially from the pages 8 and 9, which lie therein next to FIG. 1. The context of the patent at hand makes full reference to the aforementioned DE 19 912 102 A1. These electrodes are schematically reproduced in the subsequently described FIG. 1. A part of the designated electrodes form a so-called pumping cell in this sensor. The other part forms a so-called concentration cell. Furthermore, a first cavity is configured by the solid electrolyte layers (subsequently "gas measurement chamber").

A pumping voltage is applied to the electrodes of the pumping cell, by means of which in a first gas measurement chamber a constant oxygen partial pressure, i.e. a corresponding air number LAMBDA, is adjusted by additionally pumping oxygen in or out. In so doing, the pumping voltage is controlled in a closed-loop in such a way that a constant voltage value of 450 mV appears at the electrodes of the concentration cell. This voltage corresponds to a value of LAMBDA=1.

In wideband lambda sensors according to the designated double cell principle, the air number in the gas measurement chamber of the pumping cell is closed-loop controlled to a certain value, which preferably is maintained constantly at LAMBDA=1. The air number in the gas measurement chamber of the pumping cell is specified by the designated comparison voltage, which is generated by the control unit of the internal combustion engine for the Nernst cell.

A diffusion barrier lies in front of the Nernst cell. Each gas diffusing through the diffusion barrier causes a pumping current via the designated closed-loop control due to the change of the gas composition in the designated gas measurement chamber and the change of the Nernst voltage connected with it. This pumping current represents a measurement for the partial pressure difference, the diffusion coefficient and the oxygen requirement per molecule of the gas in question.

In internal combustion engines with self-ignition using afterinjection of fuel for the purpose of regenerating a particle filter disposed in the engine, the wideband sensor must be able in the lean operation to simultaneously detect the oxygen and the rich fuel. On the basis of the different diffusion coefficients of both of these gases, the relatively heavy rich gas (HC) is less significantly evaluated for its oxygen requirement as the oxygen, and as a result hydrogen is too significantly evaluated. The same is true for a mixture of rich gases, which, for example, occur in an externally-supplied ignition of an internal combustion engine in the rich operation or during regeneration of a storage catalytic converter in an internal combustion engine with self-ignition. For this reason, an evaluation of the adjusted LAMBDA-value is only possible with knowledge of the proportion of HC, respectively $H_2$. With the known lambda sensors, only the partial pressure of one of the gas components can consequently be correctly measured.

Because the known lambda sensors deliver only an output signal (and in fact the designated pumping current), the information cannot simultaneously deliver the partial pressure and the gas composition. For this reason, it is desirable to provide a procedure for the operation of one of the lambda sensors here in question. By means of this procedure, the partial pressure and the gas composition can be simultaneously determined.

SUMMARY OF THE INVENTION

The thought lying at the basis of the invention is to recognize the gas composition, respectively the type of gas delivered to a wideband lambda sensor, preferably that of an exhaust gas of an internal combustion engine, using modulated gas measurement alteration. Particularly the sensitivity of the sensor to different gases is changed periodically on account of periodic adjustment of the air number in the gas measurement chamber of the lambda sensor. In so doing, an elevation of the Nernst voltage to a value >450 mV lowers the sensitivity to rich gases, whereas a reduction of the Nernst voltage beneath the value 450 mV lowers the sensitivity to lean gases. Therefore, inference can be made in regard to a gas mixture from the reaction to the designated periodic change (modulation) of the sensitivity of the sensor whether the presence of a rich or lean component exists.

Additionally the effect lies at the basis of the invention that the diffusion coefficient for lighter molecules, respectively molecules with less of a dispersive cross-section, is greater than for heavier molecules, as the kinetic energy per variance across the smaller mass leads to a higher velocity. As a result an elevated sensitivity to smaller molecules results, because the partial pressure change in the gas measurement chamber is greater than the partial pressure difference present at both sides of the diffusion barrier.

Using the procedure according to the invention, the partial pressure of the inflowing gas and its gas composition can be simultaneously ascertained.

The procedure according to the invention allows itself, for example, to be implemented in a control unit of an internal combustion engine, especially one in a motor vehicle, in the form of a program code or a suitable electronic circuit.

BRIEF DESCRIPTION OF THE DRAWINGS

The invention is subsequently explained in more detail using the included drawings and on the basis of an example of embodiment. The following are thereby shown:

FIG. 3a-3c a typical chronological progression of the set point of the Nernst voltage, the Nernst voltage and the pumping current according to the state of the art;

DETAILED DESCRIPTION OF THE PREFERRED EMBODIMENTS

Figure 1:
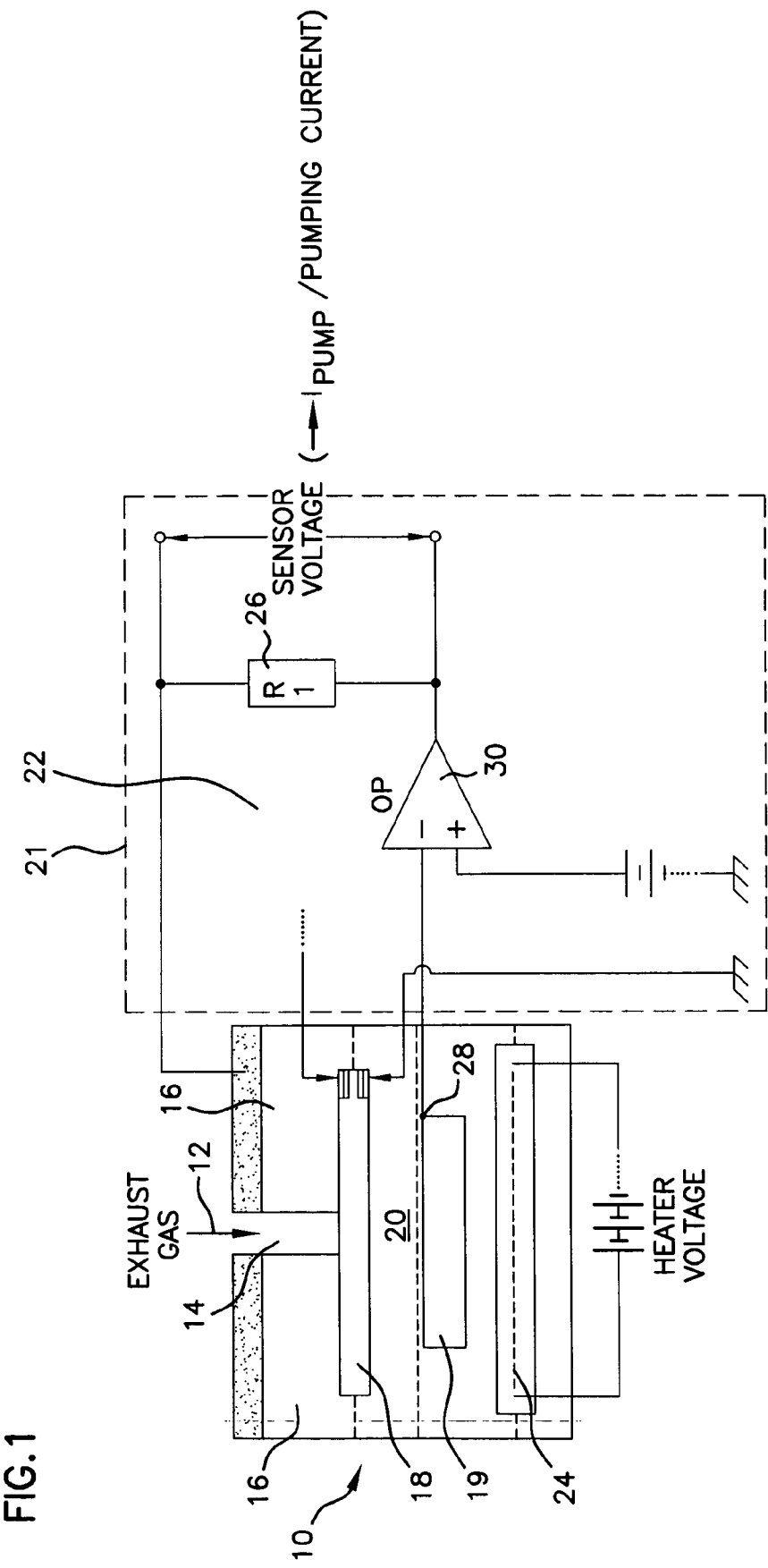
FIG. 1 schematized is an example of embodiment of a wideband lambda sensor according to the invention.

In the wideband lambda sensor 10 shown in FIG. 1, exhaust gas 12 moves through a small opening 14 of a pumping cell 16 and a (non-depicted) diffusion barrier into the actual gas measurement chamber 18 of a Nernst cell 20. A reference gas chamber 19 connects to the Nernst cell 20, in which an oxygen reference gas is contained. In the gas measurement chamber 18 a stoichiometric air-fuel-ratio is constantly set. An evaluation and control circuit 22 disposed in a control device 21 or something similar controls in a closed-loop a pumping voltage U_Pump lying at the pumping cell in such a way, that the composition of the gas in the gas measurement chamber 18 lies constantly at LAMBDA=1. In the case of lean exhaust gas 12, the pumping cell 16 pumps oxygen from the gas measurement chamber 18 to the outside. In the case of rich exhaust gas 12 the oxygen must on the other hand be pumped out of the exhaust gas 12 of the surrounding area into the gas measurement chamber; and in so doing, the direction of the electrical pumping current I_Pump must be reversed. The pumping current is in the process proportional to the oxygen concentration, respectively the oxygen requirement. In this way the pumping current I_Pump is a measurement for LAMBDA in the exhaust gas. An integrated heater 24 provides for an operating temperature of at least 600° C., which after a cold start, however, is only achieved after a certain pre-heating time.

The adjustment of the pumping current results by way of the evaluation of a control circuit 22, which compares the Nernst voltage U_Nernst with an internally generated reference voltage U_Ref of 450 mV. As soon as a deviation Delta (U_Nernst, U_Ref) exists, this deviation is reinforced in the circuit 22 and fed as the pumping current I_Pump into the pumping cell 16. Thereby oxygen is, for example, pumped out of the gas measurement chamber 18 and the Nernst voltage U_Nernst stabilizes itself at 450 mV. The necessary pumping current I_Pump or the output voltage U_Sonde, which drops across a resistor (R1) 26, is evaluated as an output signal of the sensor 10.

It is to be noted that to operate a wideband sensor 10 with a pumped reference voltage, the reference electrode is laid across a solid resistance of, for example, 100 kOhm to +5V, in order to deliver oxygen constantly to the reference gas chamber by way of the Nernst cell 20.

The output signal I_Pump is transmitted to an additional unspecified electronic control unit, which for its part signals a mixture forming device, for example, a fuel injection system or an electronically controlled carburetor, via a control signal, if the mixture has to be richened or leaned. If the mixture is too lean, more fuel is added, if the mixture is too rich, the amount of fuel delivered to the engine is again reduced.

Figure 2A:
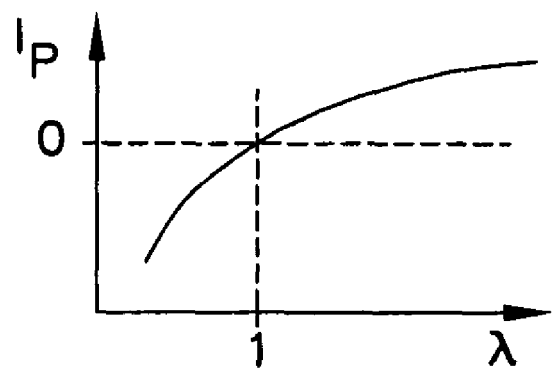
FIG. 2a a typical progression of the pumping current I_Pump as a function of LAMBDA in a wideband lambda sensor.

A typical qualitative progression of the pumping current I_Pump is shown in FIG. 2a as a function of LAMBDA. In the case of lean exhaust gas, a positive pumping current occurs, in order to maintain a stoichiometric composition with LAMBDA=1 in the gas measurement chamber. In the case of a rich exhaust gas, a negative pumping current is on the other hand present. As one is no longer here dependent on the graduated voltage characteristic of the Nernst cell, LAMBDA can be measured constantly in a range from 0.6 to infinity. A measurement for LAMBDA equaling infinity is, for example, required for the surge balancing.

Figure 2B:
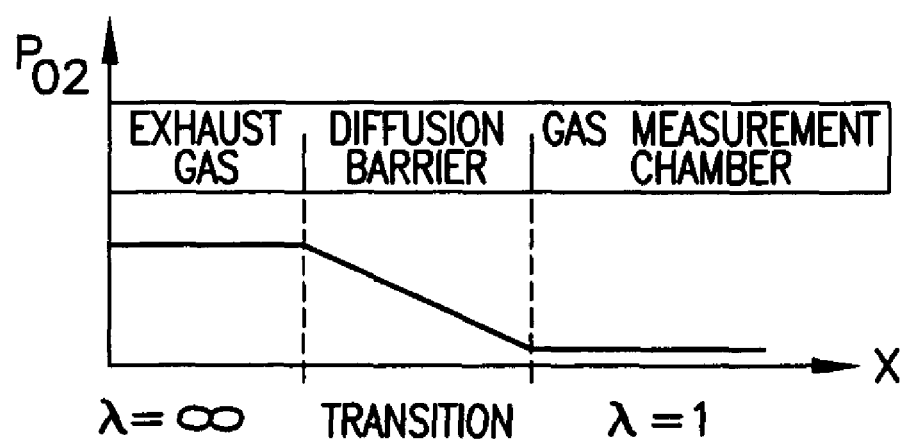
FIG. 2b a typical chronological progression of the oxygen-partial pressure in a wideband lambda sensor.

The FIG. 2b shows a typical progression of the partial pressure $p_{O2}$ of oxygen $O_2$ in a lambda sensor of a motor vehicle, in which the air value LAMBDA=1 exists in the gas measurement chamber depicted in the right hand portion of the diagram, i.e. only there a stoichiometric composition of the air-fuel-mixture arises. In the depicted external area of the lambda sensor present in the left hand side of the diagram, consequently in the exhaust gas of the internal combustion engine, a higher partial pressure $p_{O2}$ exists. Thus, there lies a value of LAMBDA=∞ (infinity). In the transition area between the exhaust gas and the gas measurement chamber, the oxygen partial pressure drops continually in a typical manner.

Figure 3B:
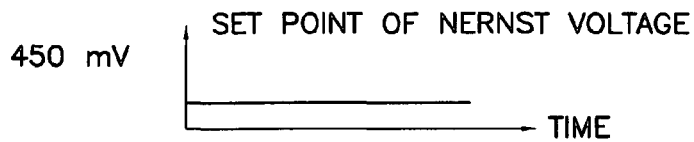
Figure 3B:
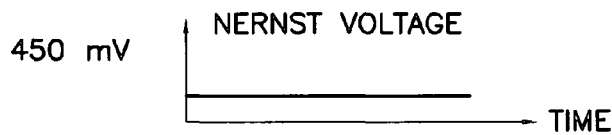
Figure 3C:
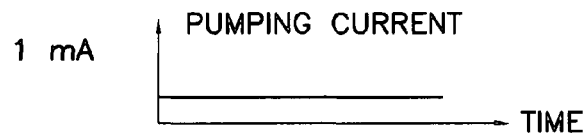

The FIGS. 3a-3c show the progression, which is known in the state of the art, of the set point of the Nernst voltage, of the final resulting Nernst voltage as well as the pumping current according to the state of the art. The FIG. 3a shows the progression of the set point of the Nernst voltage over time. In the example of embodiment, the Nernst voltage amounts to the 450 mV designated at the beginning of the application when using the lambda sensor in the area of automobile technology. It is, however, to be underscored that the concepts according to the invention also can find application in other areas of technology, for example, in the area of the chemical industry, and in fact everywhere, where exhaust gases are retreated for environmental reasons.

The FIG. 3b shows the actual resulting progression of the Nernst voltage as a function of the time and the FIG. 3c the pumping current measured in the manner described at the beginning of the application, likewise as a function of the time. During the essentially constantly progressing Nernst voltage (FIG. 3b) at hand, a likewise essentially constantly progressing pumping current results at a constant partial pressure in the exhaust gas.

Despite the modulation of the Nernst voltage and the resulting air number fluctuation, the mean value of LAMBDA in the gas measurement chamber is maintained in a preferred manner over the time at a value of preferably LAMBDA=1, which corresponds to an average Nernst voltage $U_N$ of $U_{NO}$=450 mV.

From the measured average pumping current $I_{p0}$ and the pumping current change $\Delta I_p$, it is possible, when the exhaust gas is in a sufficient steady state (i.e. no additional partial pressure fluctuations), to make an inference about the true LAMBDA-value, and in fact according to the invention independent of the respective gas composition. It is, however, to be noted, that the method at hand for gas mixtures having rich and lean components can preferably be applied to gas mixtures with gas components of differing diffusion coefficients. However, only when such gas mixtures are present, errant measurements occur as described at the beginning of the application.

Figure 4A:
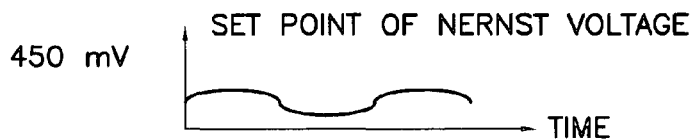
FIG. 4a-4c a chronological progression of the set point of the Nernst voltage, the Nernst voltage and the pumping current according to an example of embodiment of the procedure according to the invention to operate a lambda sensor with modulated Nernst voltage.
Figure 4B:
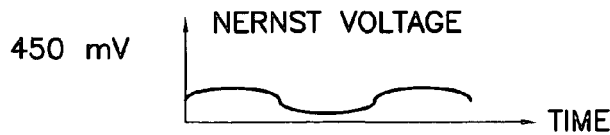
Figure 4C:
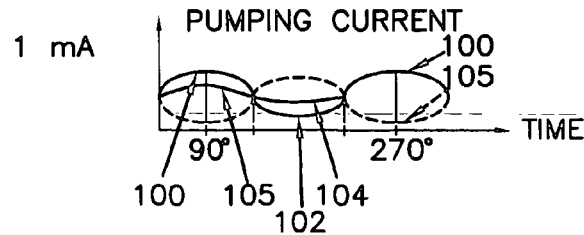

This is supposed to be clarified using the example of embodiment depicted in the FIGS. 4a-4c. In the FIG. 4a the progression of the set point of the Nernst voltage $U_N$ is depicted and in the FIG. 4b the actual progression of the Nernst voltage $U_N$. Finally, in the FIG. 4c the progression of the pumping current $I_p$ resulting from the operation according to the invention with the modulated Nernst voltage $U_N$ according to FIGS. 4a and 4b is depicted.

The set point of the Nernst voltage $U_N$ (FIG. 4a) is sinusoidally modulated with an average frequency from 1 Hz to 20 Hz, preferably with 5 Hz. The amplitude of the modulated signal amounts thereby to 25 mV to 450 mV, preferably, however, 100 mV. The signal synchronous to the progression of the Nernst voltage $U_N$ (i.e. that caused by energization of the pumping current $I_p$) is used as the output signal as in the state of the art. Additionally inference is made about the gas composition from the amplitude of the pumping current fluctuation $\Delta I_p$, i.e. from the average fluctuation of the pumping current $I_p$ at 90° and at 270°, using the designated manner of calculation, and together with that in the result, the output signal of the lambda sensor is converted into an actual LAMBDA-value.

The progression of the pumping current $I_p$ depicted in FIG. 4c varies in the manner shown there and in fact as a function of the gas mixture to be detected in each case. In the case of the detection of the lighter rich gas, the progression 100 results, whereas during the detection of the heavier rich gas, the progression as a dashed line results. Using the progression of the measurement curve in the range of the phase 180°, oxygen ($O_2$) is detected 102. Using the alternative progressions 104, 105 of the pumping current $I_p$, lean gas 104 and/or heavy rich gas is able to be detected.

Figure 5A:
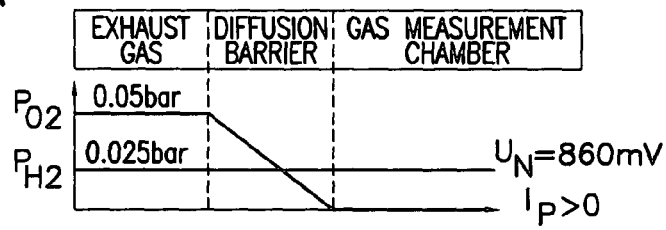
FIG. 5a-5c partial pressure progressions of hydrogen and oxygen as examples to illustrate the determination of the relative gas compositions according to invention from both of the diffusing gases: hydrogen and oxygen.
Figure 5B:
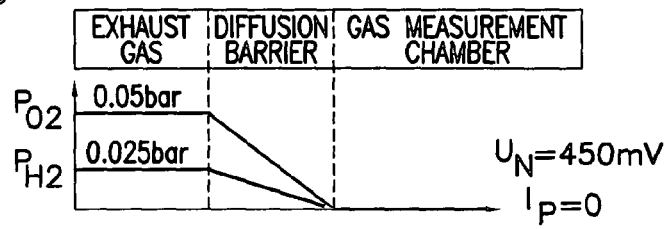
Figure 5C:
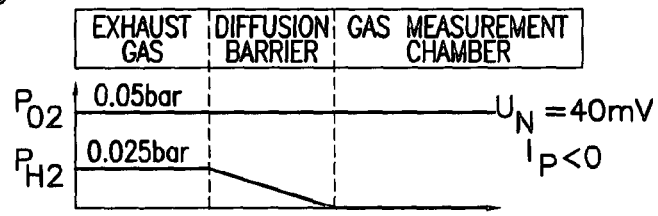

In an exhaust gas aftertreatment in an internal combustion engine, two gases are preferably concerned, namely a combination of a lighter additional gas with oxygen, preferably hydrogen ($H_2$), or a combination of a heavier additional gas with oxygen ($O_2$), preferably HC. As mentioned at the beginning of the application, the value of the air number LAMBDA in the gas measurement chamber is periodically altered and the corresponding alteration to the pumping current is detected (FIGS. 4a-4c). From the resulting, likewise periodic progression of the pumping current signal, the gas composition from both of the diffusing gases is able to be determined according to the invention, as subsequently described using the FIGS. 5a-5c.

The starting situation would represent a gas mixture, in the example of embodiment at hand $H_2+O_2$, which delivers a stable LAMBDA-value, preferably with an associated pumping current $I_p$=0 as an output signal. This pumping current value is interpreted as LAMBDA=1, whereby it is furthermore assumed that the ratio $D_{O2}:D_{H2}$ of the diffusion constants of oxygen and hydrogen is equal to 1 in the designated diffusion barrier.

As soon as the Nernst voltage $U_N$ is increased on account of the modulation, a rich mixture arises by pumping out $O^{2-}$-ions in the gas measurement chamber. This means that an elevated hydrogen partial pressure $p_{H2}$ is present. In so doing, the partial pressure gradient $\Delta p$, which drives the incoming diffusion, is smaller for $H_2$ but remains at least essentially the same for $O_2$.

In the statistical borderline case, $O^{2-}$-ions must accordingly be pumped out of the gas measurement chamber, instead of the reciprocally compensating H2 and $O_2$-incoming diffusions into the gas measurement chamber. A positive pumping current in the positive modulation half-wave of the Nernst voltage $U_N$ indicates as a result a rich component in the mixture.

As soon as the Nernst voltage $U_N$ is reduced (FIG. 5c), the partial pressure $p_{O2}$ for oxygen increases in the gas measurement chamber. The partial pressure difference $\Delta p_{O2}$ decreases thereby, so that only $H_2$ diffuses into the gas measurement chamber. This requires again a negative pumping current. This negative pumping current in the negative half-wave indicates accordingly a lean component in the gas mixture.

In the borderline case of a gas mixture having only oxygen $O_2$ with LAMBDA=1, only the previously mentioned negative pumping current $I_p$ would appear, however not a positive pumping current $I_p$ at an increased Nernst voltage $U_N$. Only the amplitude of the curve 102 would be correspondingly smaller in this case on account of the lower value of $p_{O2}$ at LAMBDA=1.

If on the other hand a gas mixture with LAMBDA=1 is present, which is composed of a HC-molecule and hydrogen $H_2$, this mixture then has an increased partial pressure $p_{HC}$, because the required $O_2$-gas is transported in slower due to the relatively small diffusion coefficient. For this reason, in the example of embodiment according to FIG. 5a, in which an increased Nernst voltage $U_N$ is assumed, the increase in the partial pressure is only partially slowed down by the incoming diffusion of HC-gas. For this reason, the increase in the pumping current $I_p$ breaks down less with heavy molecules.

In the case of a decreased Nernst voltage $U_N$, the unchanged ratios described above using FIG. 5c are present. A small reaction of a positive pumping current $I_p$ in the positive half-wave indicates then a heavy rich gas component.

Figure 6A:
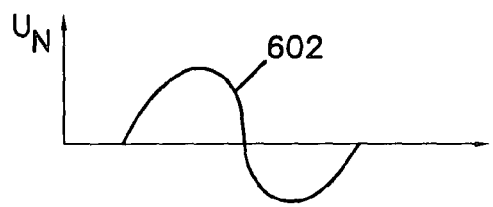
FIG. 6a, b progressions of the Nernst voltage UN and the pumping currents $I_p$ resulting from it as examples for the different gas components of a typical exhaust gas of an internal combustion engine of a motor vehicle and in fact for the generalized application case with LAMBDA≠1
Figure 6B:
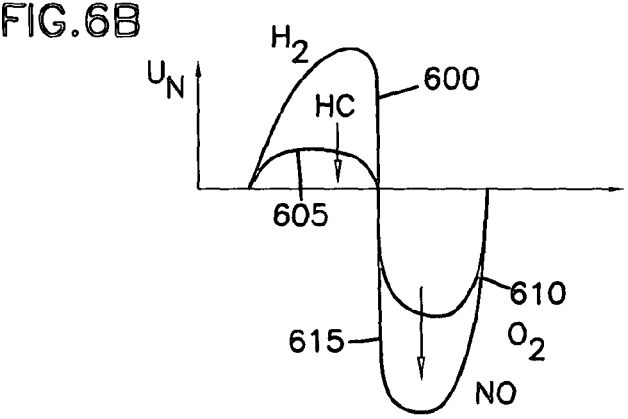

The analogous case is true for differentially heavy lean components, than most certainly for the negative pumping current $I_p$ in the negative half-wave. Generally the subsequently described contexts result for gas mixtures with LAMBDA$\neq$1 according to the FIGS. 6a and 6b. The starting situation is again a gas mixture, in the example of embodiment at hand consisting of $H_2$, $O_2$, HC and NO. The FIG. 6a shows the time modulated (in the Figure at hand sinusoidal)

progression 602 of the Nernst voltage $U_N$. An increased Nernst voltage $U_N$ lying at the gas measurement chamber according to the first half-wave in FIG. 6*a* leads in this example of embodiment, which can be understood in FIG. 6*b*, to a drop in the pumping current 605 of heavier HC as compared to the pumping current 600 for the lighter $H_2$-gas. Correspondingly a lowered Nernst voltage $U_N$ leads according to the second half-wave in FIG. 6*a* to a lowered pumping current 615 for NO (FIG. 6*b*) as compared to the pumping current 610 for $O_2$, i.e. resulting from a smaller $O_2$ requirement in the gas measurement chamber.

The invention claimed is:

1. A method of recognizing a gas composition of a gas mixture of an exhaust gas of an internal combustion engine of a motor vehicle, which consists of at least two gases of preferably different diffusion properties, delivered to a wideband lambda sensor, wherein the lambda sensor has a pumping cell with at least one gas measurement chamber, the method comprising:

chronologically modulating a Nernst voltage of the lambda sensor to infer the gas composition of the gas mixture delivered to the at least one gas measurement chamber.

2. A method according to claim 1, further comprising periodically altering an air number in the gas measurement chamber of the pumping cell, whereby the sensitivity of the lambda sensor for the gases, of which there are at least two, likewise periodically changes.

3. A method according to claim 1, wherein modulating includes modulating the Nernst voltage in a chronological sinusoidal manner.

4. A method according to claim 3, wherein modulating includes modulating the Nernst voltage in such a way that the chronological mean value of the air number LAMBDA=1 arises.

5. A method according to claim 3, wherein modulating includes sinsusoidally modulating the Nernst voltage with a frequency from 1 Hz to 20 Hz, preferably with 5 Hz, wherein an amplitude of the modulated signal amounts to between 25 m V and 450 m V, preferably 100 m V.

6. A method according to claim 1, further comprising evaluating a pumping current, which operates essentially synchronously to the Nernst voltage, and the amplitude of a pumping current fluctuation.

7. A method according to claim 6, further comprising inferring the gas composition from an average fluctuation of the pumping current at at least two angle values of a periodic progression of the Nernst voltage, preferably at 90° and at 270°, and converting a measured pumping current into a real LAMBDA-value.

8. A method according to claim 1, further comprising inferring the gas composition from an average fluctuation of a pumping current at least two angle values of a periodic progression of a Nernst voltage, and converting the measured pumping current into a real LAMBDA-value.

9. A control unit to operate a wideband lambda sensor, characterized by a control program to determine a gas composition of a gas mixture of an exhaust gas of an internal combustion engine of a motor vehicle delivered to a wideband lambda sensor, wherein the lambda sensor has a pumping cell with at least one gas measurement chamber, wherein the control unit is configured to chronologically modulate a Nernst voltage of the lambda sensor to infer the gas composition of the gas mixture delivered to the at least one gas measurement chamber of the lambda sensor.

10. A control unit according to claim 9, wherein the control unit periodically alters an air number in the gas measurement chamber of the pumping cell, whereby the sensitivity of the lambda sensor for the gases, of which there are at least two, likewise periodically changes.

\* \* \* \* \*